US00PP26839P2

(12) United States Plant Patent
Zaiger et al.

(10) Patent No.: US PP26,839 P2
(45) Date of Patent: Jun. 21, 2016

(54) PEACH TREE NAMED 'SAUZEE JEWEL'

(50) Latin Name: *Prunus persica*
Varietal Denomination: Sauzee Jewel

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 52 days.

(21) Appl. No.: 14/544,256

(22) Filed: Dec. 15, 2014

(51) Int. Cl.
*A01H 5/08* (2006.01)

(52) U.S. Cl.
USPC ..... Plt./195

(58) Field of Classification Search
USPC ..... Plt./195
See application file for complete search history.

*Primary Examiner* — Anne Grunberg

(57) ABSTRACT

A new and distinct variety of peach tree (*Prunus persica*). The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree with vigorous, upright growth.
2. Regular and productive bearer of large size fruit.
3. Fruit with an attractive red blush skin color.
4. Fruit with very good flavor and eating quality.
5. Fruit with good storage and handling quality.
6. Fruit with firm, white flesh.

1 Drawing Sheet

Botanical designation: *Prunus persica.*
Variety denomination: 'Sauzee Jewel'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was, against this background of our activities that the present variety of peach tree was originated and asexually reproduced by us in our experimental orchard located near Modesto, Stanislaus County, Calif.

PRIOR VARIETIES

Among the existing varieties of peach trees, which are known to us, and mentioned herein are 'September Snow' Peach (U.S. Plant Pat. No. 8,003) and our proprietary non-patented peach seedling selections with the field identification numbers '220LV352', '358LN87' and '30LR286'.

STATEMENT REGARDING FEDERALLY SPONSORED RESEARCH AND DEVELOPMENT

Not applicable.

ORIGIN OF THE VARIETY

The new and distinct variety of peach tree (*Prunus persica*) was developed by us in our experimental orchard located near Modesto, Calif. from an open pollinated seed collected from our proprietary non-patented peach seedling selection with the field identification number '220LV352'. The seed parent (220LV352) originated from a cross between our proprietary non-patented peach seedling selections '358LN87' and '30LR286'. A large group of these open pollinated seedlings were planted and maintained on their own root system, during which time we recognized the desirable tree and fruit characteristics of the present seedling and selected it in 2008 for additional asexual propagation and commercialization.

ASEXUAL REPRODUCTION OF THE VARIETY

In 2008 asexual reproduction of the new and distinct variety of peach tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new variety of peach tree (*Prunus persica*) is of large size, vigorous upright growth and is a productive and regular bearer of large size, white flesh, clingstone fruit. The fruit is further characterized as being peen-to in shape, having mild, sweet, sub-acid flavor with very good eating quality. In comparison to the proprietary peach seed parent '220LV352' (non-patented) the fruit of the new variety has white flesh compared to yellow and is approximately 17 days later in maturity. In comparison to the commercial variety 'September Snow' Peach (U.S. Plant Pat. No. 8,003) the fruit of the new variety is peen-to in shape compared to globose and is approximately 6 days later in maturity.

DESCRIPTION OF PHOTOGRAPH

The accompanying color photographic illustration shows typical specimens of the foliage and fruit of the present new peach variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 6 year old tree and the colors are as nearly true as is reasonably possible in a color representation of this type.

DESCRIPTION OF THE VARIETY

The following is a detailed botanical description of the new variety of peach tree, its flowers, foliage and fruit, as based on observations of 6 year old specimens grown near Modesto, Calif., with color in accordance with Munsell Book of Color published in 1958.

Tree:

*Size*.—Large, usually pruned to 3 to 3.5 meters in height and width for economical harvesting of fruit. Size varies with different cultural practices.

*Vigor*.—Vigorous, growth of 1.5 to 2 meters the first growing season. Varies slightly with type and fertility of soil, climatic conditions and cultural practices.

*Form*.—Upright, usually pruned to vase shape.

*Branching habit*.—Upright, crotch angle approximately 35°, increases with heavy crop load.

*Productivity*.—Productive, thinning and spacing necessary for desired market size fruit. Number of fruit set varies with climatic conditions during blooming period.

*Bearer*.—Regular, has had adequate fruit set 4 consecutive years. No alternate bearing observed.

*Fertility*.—Self fertile.

*Density*.—Medium dense, usually pruned to vase shape to increase air movement and sunlight to enhance fruit color and health of fruit wood.

*Hardiness*.—Hardy in all stone fruit growing areas of California. Tree grown in USDA Hardiness Zone 9. Winter chilling requirement approximately 950 hours at or below 45° F.

Trunk:

*Size*.—Medium. Average circumference 56.8 cm at 19.9 cm above ground on a 6 year old tree.

*Stocky*.—Medium stocky.

*Texture*.—Medium shaggy, roughness increases with age.

*Color*.—Varies from 2.5Y 3/2 to 5Y 4/2.

Branches:

*Size*.—Medium to large. Average circumference 16.5 cm at 1.2 meters above ground on a 6 year old tree. Crotch angle approximately 35°, increases with heavy crop load.

*Surface texture*.—New growth relatively smooth. Mature growth medium rough, roughness increases with age.

*Lenticels*.—Average number 48 in 25.8 sq cm area. Average length 3.4 mm. Average width 2.0 mm. Color varies from 7.5YR 5/8 to 10YR 5/8.

*Color*.—New growth varies from 2.5GY 6/6 to 5GY 6/6. Mature growth varies from 10YR 3/4 to 2.5Y 3/4, varies with age of growth.

Leaves:

*Size*.—Large. Average length 135.9 mm. Average width 35.0 mm.

*Form*.—Lanceolate.

*Apex*.—Acuminate.

*Base*.—Cuneate.

*Margin*.—Crenate.

*Thickness*.—Medium.

*Surface texture*.—Upper surface relatively smooth, slightly indented over midrib and leaf veins, glabrous. Lower surface relatively smooth except for small ridges created by midrib and pinnate venation, glabrous.

*Petiole*.—Average length 10.9 mm. Average width 1.2 mm. Longitudinally grooved. Surface — glabrous. Color varies from 5GY 6/6 to 5GY 5/6.

*Glands*.—Type — reniform. Size — small. Average length 1.0 mm. Average diameter 0.5 mm. Average number 3, varies from 1 to 5. Located primarily on base of leaf blade and upper portion of petiole. Color varies from 5GY 5/6 with 10R 3/6.

*Stipules*.—Average number 2. Average length 5.4 mm. Edges — pectinate. Color varies from 5GY 8/6 to 10R 3/4.

*Color*.—Upper surface 7.5GY 4/4. Lower surface varies from 5GY 5/4 to 5GY 4/6. Midvein color varies from 5GY 8/6 to 5GY 7/6.

Flower Buds:

*Size*.—Large. Average length 20.3 mm. Average diameter 10.3 mm.

*Hardiness*.—Hardy with respect to California winters.

*Density*.—Medium dense.

*Form*.—Elongated.

*Pedicel*.—Average length 5.3 mm. Average width 1.5 mm. Color varies from 2.5GY 7/4 to 2.5GY 7/6. Surface glabrous.

*Color*.—Varies from 5RP 7/8 to 5RP 8/6.

Flowers:

*Blooming period*.—Date of First Bloom Mar. 3, 2014. Date of Petal Fall Mar. 12, 2014, varies slightly with climatic conditions.

*Size*.—Large, showy. Average height 25.0 mm. Average diameter 47.6 mm.

*Petals*.—Normally 5, alternately arranged to sepals. Size — large. Average length 24.6 mm. Average width 20.1 mm. Form — ovate. Petal apex — rounded. Petal base — acuminate. Arrangement — free. Margin — sinuate. Color varies from 5RP 7/6 to 5RP 7/10, color fades with age of flower. Both upper and lower surfaces glabrous.

*Sepals*.—Normally 5, alternately arranged to petals. Size — large. Average length 6.4 mm. Average width 5.4 mm. Shape — triangular. Apex — rounded to triangular. Margin — entire. Surface — upper surface glabrous, lower surface pubescent. Color — upper surface varies from 5GY 5/6 to 5R 3/6. Lower surface varies from 5R 2/6 to 5R 2/8.

*Stamens*.—Average number per flower 37, varies from 36 to 39. Average filament length 15.8 mm. On average, the stamens are even with the height of the petals. Filament color varies from N 9.5/ (white) to 5RP 8/4. Anther color varies from 10R 4/12 to 5Y 9/6.

*Pollen*.—Self fertile. Color varies from 2.5Y 8/4 to 2.5Y 7/12.

*Pistil*.—Normally 1. Surface — pubescent. Average length 16.8 mm. Position of stigma an average of 1.0 mm below anthers. Color varies from 5Y 8.5/6 to 5Y 8.5/12.

*Fragrance*.—Moderate.

*Color*.—Varies from 5RP 7/8 to 5RP 8/6.

*Number flowers per flower bud*.—Normally one.

*Pedicel*.—Average length 5.6 mm. Average width 1.5 mm. Color varies from 5GY 6/6 to 7.5R 2/8. Surface glabrous.

Fruit:

*Maturity when described*.—Firm ripe and ready for consumption.

*Date of first picking*.—Sep. 1, 2014.

*Date of last picking*.—Sep. 11, 2014, varies slightly with climatic conditions.

*Size*.—Large. Average diameter axially 44.2 mm. Average transversely in suture plane 79.4 mm. Average weight 187.4 grams, varies slightly with fertility of the soil, amount of thinning and climatic conditions.

*Form*.—Flat, peen-to shape.

*Suture*.—Lipped, extends from base to apex.

*Ventral surface*.—Lipped, well sealed.

*Apex*.—Retuse.

*Base*.—Retuse.

*Stem cavity*.—Rounded to slightly elongated in suture plane. Average depth 5.8 mm. Average length 9.3 mm.

Stem:

*Size*.—Small to medium. Average length 9.5 mm. Average diameter 2.7 mm.

*Color*.—Varies from 5GY 6/8 to 5GY 5/8.

Flesh:

*Ripens*.—Evenly.

*Texture*.—Firm, meaty.

*Fibers*.—Few, small, tender.

*Firmness*.—Firm, comparable to other commercial varieties.

*Aroma*.—Heavy.

*Amydgalin*.—Undetected.

*Eating quality*.—Very good.

*Flavor*.—Very good, mild, sweet, sub-acid flavor.

*Juice*.—Heavy amount, enhances flavor.

*Brix*.—Average Brix 13.6°, varies slightly with amount of fruit per tree and climatic conditions.

*Color*.—Varies from 5Y 9/4 to 7.5Y 9/2.

*Pit cavity*.—Average length 19.0 mm. Average width 25.9 mm. Average depth 12.0 mm. Color varies from 7.5R 3/8 to 7.5R 3/12.

Skin:

*Thickness*.—Medium.

*Surface*.—Smooth.

*Pubescence*.—Moderate amount, very short.

*Tendency to crack*.—None.

*Color*.—Ground color varies from 7.5Y 9/4 to 7.5Y 9/6. Overspread with 5R 3/6 to 5R 3/8.

*Tenacity*.—Tenacious to flesh.

*Astringency*.—Undetected.

Stone:

*Type*.—Clingstone, adherence to flesh strong.

*Size*.—Medium. Average length 18.2 mm. Average width 24.9 mm. Average thickness 20.2 mm.

*Form*.—Globose.

*Base*.—Flat.

*Apex*.—Flat.

*Surface*.—Pitted throughout, pits vary from round to elongated.

*Sides*.—Unequal, one side extending further from suture plane.

*Ridges*.—Relatively smooth, extending from base to apex.

*Tendency to split*.—None.

*Color*.—7.5R 2/4 when dry.

Kernel:

*Size*.—Medium. Average length 9.1 mm. Average width 10.3 mm. Average depth 7.4 mm.

*Form*.—Globose.

*Viability*.—Viable, complete embryo development.

*Skin color*.—Varies from 2.5Y 8/6 to 5Y 9/4.

Use:

*Dessert*. Market — local and long distance.

Keeping Quality: Good, held firm in cold storage at 38° to 42° F. for 3 weeks without internal breakdown of flesh or appreciable loss of flavor.

Shipping Quality: Good, minimal skin scarring or bruising of flesh during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program. Not atypical resistances/susceptibilities have been noted under normal cultural practices.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of peach tree (*Prunus persica*), substantially as illustrated and described.

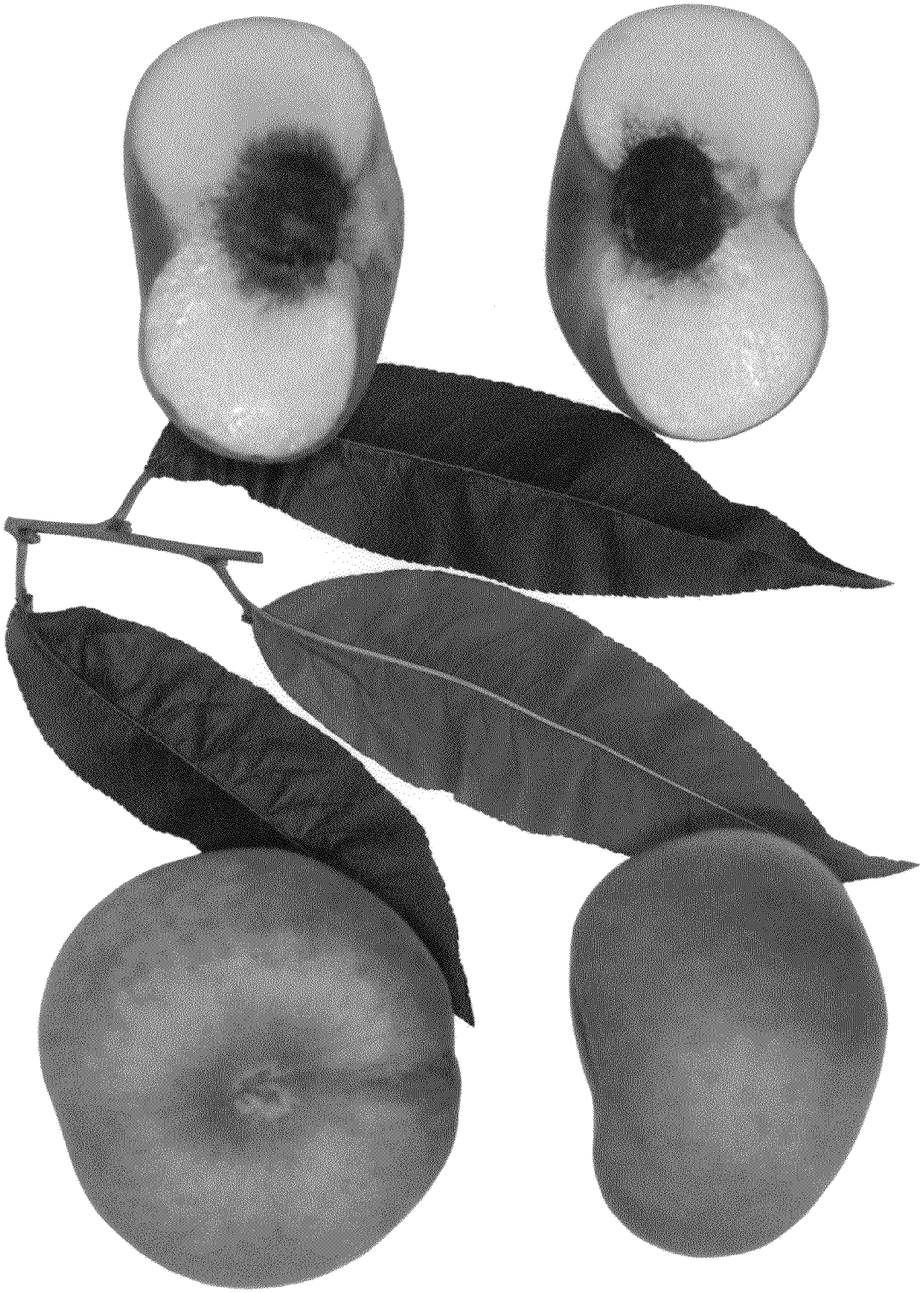

* * * * *